United States Patent
Nelson et al.

(10) Patent No.: US 10,377,890 B2
(45) Date of Patent: *Aug. 13, 2019

(54) NANOCELLULOSE-POLYSTYRENE COMPOSITES

(71) Applicant: API Intellectual Property Holdings, LLC, Atlanta, GA (US)

(72) Inventors: Kimberly Nelson, Atlanta, GA (US); Asis Kumar Banerjie, Medina, OH (US); Theodora Retsina, Atlanta, GA (US)

(73) Assignee: GranBio Intellectual Property Holdings, LLC, Atlanta, GA (US)

( * ) Notice: Subject to any disclaimer, the term of this patent is extended or adjusted under 35 U.S.C. 154(b) by 185 days.

This patent is subject to a terminal disclaimer.

(21) Appl. No.: 15/189,040

(22) Filed: Jun. 22, 2016

(65) Prior Publication Data

US 2017/0015822 A1    Jan. 19, 2017

Related U.S. Application Data

(63) Continuation-in-part of application No. 14/750,961, filed on Jun. 25, 2015, now abandoned.

(60) Provisional application No. 62/183,672, filed on Jun. 23, 2015, provisional application No. 62/109,425, filed on Jan. 29, 2015, provisional application No. 62/069,417, filed on Oct. 28, 2014, provisional application No. 62/018,337, filed on Jun. 27, 2014.

(51) Int. Cl.
| | |
|---|---|
| *C08L 1/02* | (2006.01) |
| *C08L 25/06* | (2006.01) |
| *D21H 11/18* | (2006.01) |
| *D21H 19/52* | (2006.01) |
| *D21H 19/56* | (2006.01) |
| *D21H 21/18* | (2006.01) |
| *D21H 19/22* | (2006.01) |
| *D21H 19/34* | (2006.01) |
| *B82Y 30/00* | (2011.01) |
| *C08H 8/00* | (2010.01) |
| *D21H 17/35* | (2006.01) |
| *D21H 17/00* | (2006.01) |
| *C12P 19/02* | (2006.01) |
| *C12P 7/10* | (2006.01) |

(52) U.S. Cl.
CPC ............ *C08L 25/06* (2013.01); *B82Y 30/00* (2013.01); *C08H 8/00* (2013.01); *C08L 1/02* (2013.01); *D21H 11/18* (2013.01); *D21H 17/35* (2013.01); *D21H 17/72* (2013.01); *D21H 19/22* (2013.01); *D21H 19/34* (2013.01); *D21H 19/52* (2013.01); *D21H 19/56* (2013.01); *D21H 21/18* (2013.01); *C08L 2205/16* (2013.01); *C12P 7/10* (2013.01); *C12P 19/02* (2013.01)

(58) Field of Classification Search
None
See application file for complete search history.

(56) References Cited

U.S. PATENT DOCUMENTS

2013/0273350 A1* 10/2013 Lee .................. D06M 15/05
                                                    428/326
2015/0232703 A1*  8/2015 Nelson ............ C09D 197/005
                                                    435/99

* cited by examiner

*Primary Examiner* — Sheeba Ahmed
(74) *Attorney, Agent, or Firm* — O'Connor & Company; Ryan P. O'Connor

(57) ABSTRACT

A new polystyrene-nanocellulose composite material is disclosed. The composite may contain about 0.01 wt % to about 10 wt %, such as about 0.1 wt % to about 2 wt % of nanocellulose. In some embodiments, the nanocellulose is lignin-coated nanocellulose, such as lignin-coated nanocellulose is obtained from an AVAP® biomass-fractionation process. The nanocellulose may include cellulose nanocrystals and/or cellulose nanofibrils. The polymer composite may be in the form of a polymer melt, or a finished polymer material. The composite is characterized by IZOD impact resistance that is at least 50% (such as 75% or more) higher compared to the polystyrene alone.

9 Claims, No Drawings

NANOCELLULOSE-POLYSTYRENE COMPOSITES

PRIORITY DATA

This patent application is a non-provisional application claiming priority to U.S. Provisional Patent App. No. 62/183,672, filed Jun. 23, 2015, which is hereby incorporated by reference herein. This application is also a continuation-in-part of U.S. patent application Ser. No. 14/750,961, filed on Jun. 25, 2015, which is hereby incorporated by reference herein.

FIELD

The present invention generally relates to polymers, polymer composites, and polymer processing.

BACKGROUND

Biomass refining (or biorefining) has become more prevalent in industry. Cellulose fibers and sugars, hemicellulose sugars, lignin, syngas, and derivatives of these intermediates are being utilized for chemical and fuel production. Indeed, we now are observing the commercialization of integrated biorefineries that are capable of processing incoming biomass much the same as petroleum refineries now process crude oil. Underutilized lignocellulosic biomass feedstocks have the potential to be much cheaper than petroleum, on a carbon basis, as well as much better from an environmental life-cycle standpoint.

Lignocellulosic biomass is the most abundant renewable material on the planet and has long been recognized as a potential feedstock for producing chemicals, fuels, and materials. Lignocellulosic biomass normally comprises primarily cellulose, hemicellulose, and lignin. Cellulose and hemicellulose are natural polymers of sugars, and lignin is an aromatic/aliphatic hydrocarbon polymer reinforcing the entire biomass network. Some forms of biomass (e.g., recycled materials) do not contain hemicellulose.

Despite being the most available natural polymer on earth, it is only recently that cellulose has gained prominence as a nanostructured material, in the form of nanocrystalline cellulose (NCC), nanofibrillar cellulose (NFC), and bacterial cellulose (BC). Nanocellulose is being developed for use in a wide variety of applications such as polymer reinforcement, antimicrobial films, biodegradable food packaging, printing papers, pigments and inks, paper and board packaging, barrier films, adhesives, biocomposites, wound healing, pharmaceuticals and drug delivery, textiles, water-soluble polymers, construction materials, recyclable interior and structural components for the transportation industry, rheology modifiers, low-calorie food additives, cosmetics thickeners, pharmaceutical tablet binders, bioactive paper, pickering stabilizers for emulsion and particle stabilized foams, paint formulations, films for optical switching, and detergents.

Biomass-derived pulp may be converted to nanocellulose by mechanical processing. Although the process may be simple, disadvantages include high energy consumption, damage to fibers and particles due to intense mechanical treatment, and a broad distribution in fibril diameter and length.

Biomass-derived pulp may be converted to nanocellulose by chemical processing. For example, pulp may be treated with 2,2,6,6-tetramethylpiperidine-1-oxy radical (TEMPO) to produce nanocellulose. Such a technique reduces energy consumption compared to mechanical treatment and can produce more uniform particle sizes, but the process is not regarded as economically viable.

Improved processes for producing nanocellulose from biomass at reduced energy costs are needed in the art. Also, improved starting materials (i.e., biomass-derived pulps) are needed in the art for producing nanocellulose. It would be particularly desirable for new processes to possess feedstock flexibility and process flexibility to produce either or both nanofibrils and nanocrystals, as well as to co-produce sugars, lignin, and other co-products. For some applications, it is desirable to produce nanocellulose with high crystallinity, leading to good mechanical properties of the nanocellulose or composites containing the nanocellulose. For certain applications, such as nanocellulose-polymer composite materials, it would be beneficial to increase the hydrophobicity of the nanocellulose.

High-impact polystyrene (HIPS) is a low-cost plastic material that is easy to machine and fabricate. HIPS is often specified for structural applications when impact resistance, machinability, and low cost are required. It is frequently used machining pre-production prototypes since it has excellent dimensional stability and is easy to fabricate, paint and glue. Applications include medical packaging, food trays and containers, electronics, lids, plates, trays, patterns, and forms. Improvements to HIPS are desired.

SUMMARY

In some variations, the invention provides a polymer composite comprising polystyrene and hydrophobic nanocellulose. The composite may contain about 0.01 wt % to about 10 wt % of the nanocellulose, or about 0.05 wt % to about 5 wt % of the nanocellulose, or about 0.1 wt % to about 2 wt % of the nanocellulose.

In some embodiments, the nanocellulose is lignin-coated nanocellulose, such as lignin-coated nanocellulose is obtained from an AVAP® biomass-fractionation process. The nanocellulose may include cellulose nanocrystals and/or cellulose nanofibrils.

The polymer composite may be in the form of a polymer melt, a finished polymer material, an intermediate material, and so on.

In preferred embodiments, the composite is characterized by IZOD impact resistance that is at least 50% higher compared to the polystyrene alone.

DETAILED DESCRIPTION OF SOME EMBODIMENTS

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with any accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. All composition numbers and ranges based on percentages are weight percentages, unless indicated otherwise. All ranges of numbers or conditions are meant to encompass any specific value contained within the range, rounded to any suitable decimal point.

Unless otherwise indicated, all numbers expressing parameters, reaction conditions, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phrase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" limits the scope of a claim to the specified elements or method steps, plus those that do not materially affect the basis and novel characteristic(s) of the claimed subject matter.

With respect to the terms "comprising," "consisting of" and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

Generally it is beneficial to process biomass in a way that effectively separates the major fractions (cellulose, hemicellulose, and lignin) from each other. The cellulose can be subjected to further processing to produce nanocellulose. Fractionation of lignocellulosics leads to release of cellulosic fibers and opens the cell wall structure by dissolution of lignin and hemicellulose between the cellulose microfibrils. The fibers become more accessible for conversion to nanofibrils or nanocrystals. Hemicellulose sugars can be fermented to a variety of products, such as ethanol, or converted to other chemicals. Lignin from biomass has value as a solid fuel and also as an energy feedstock to produce liquid fuels, synthesis gas, or hydrogen; and as an intermediate to make a variety of polymeric compounds. Additionally, minor components such as proteins or rare sugars can be extracted and purified for specialty applications.

This disclosure describes processes and apparatus to efficiently fractionate any lignocellulosic-based biomass into its primary major components (cellulose, lignin, and if present, hemicellulose) so that each can be used in potentially distinct processes. An advantage of the process is that it produces cellulose-rich solids while concurrently producing a liquid phase containing a high yield of both hemicellulose sugars and lignin, and low quantities of lignin and hemicellulose degradation products. The flexible fractionation technique enables multiple uses for the products. The cellulose is an advantaged precursor for producing nanocellulose, as will be described herein.

In some variations, the invention provides a polymer composite comprising polystyrene and hydrophobic nanocellulose. The composite may contain about 0.01 wt % to about 10 wt % of the nanocellulose, or about 0.05 wt % to about 5 wt % of the nanocellulose, or about 0.1 wt % to about 2 wt % of the nanocellulose.

In some embodiments, the nanocellulose is lignin-coated nanocellulose, such as lignin-coated nanocellulose is obtained from an AVAP® biomass-fractionation process. The nanocellulose may include cellulose nanocrystals and/or cellulose nanofibrils.

The polymer composite may be in the form of a polymer melt, a finished polymer material, an intermediate material, and so on.

In preferred embodiments, the composite is characterized by IZOD impact resistance that is at least 50% higher compared to the polystyrene alone.

In some embodiments, the nanocellulose includes hydrophobic nanocellulose. In these or other embodiments, wherein the nanocellulose includes hydrophilic nanocellulose. In certain embodiments, the nanocellulose includes lignin-coated cellulose nanocrystals and/or lignin-coated cellulose nanofibrils.

The nanocellulose may be obtained from an AVAP® lignocellulosic biomass fractionation process. In some embodiments, the nanocellulose is obtained from fractionation of lignocellulosic biomass in the presence of an acid catalyst, a solvent for lignin, and water, to generate cellulose-rich solids, following by mechanical treatment of the cellulose-rich solids to generate the hydrophobic nanocellulose or a precursor thereof. The acid catalyst may be a sulfur-containing compound, such as a compound is selected from the group consisting of sulfur dioxide, sulfurous acid, sulfur trioxide, sulfuric acid, elemental sulfur, sulfonic acids, lignosulfonic acids, and combinations thereof. The solvent for lignin may be an aliphatic alcohol.

The nanocellulose may be present in the melt phase at a concentration of about 0.01 wt % to about 10 wt %, such as about 0.05 wt % to about 5 wt %, or about 0.1 wt % to about 2 wt %.

In some embodiments, the nanocellulose is combined with the polymer or a combination of polymers prior to forming the melt phase. For example, the nanocellulose may be combined with the polymer or a combination of polymers in the form of a blend, masterbatch, pellet, or powder.

In some embodiments, the nanocellulose is combined with the polymer or a combination of polymers while forming the melt phase. For example, the nanocellulose may be introduced to the melt phase in the form of a blend, masterbatch, pellet, or powder containing both the hydrophobic nanocellulose and the polymer or a combination of polymers. In some embodiments, the nanocellulose is combined with the melt phase.

The method further may include introducing one or more additives selected from the group consisting of compatibilizers, plasticizers, antioxidants, colorants, flame retardants, elastomers, ionomers and combinations thereof.

The method further may include introducing one or more additives selected from the group consisting of fillers and fibers, such as clay, nano-clay, talc, wollastonite, calcium carbonate, silica, mica, glass fibers, carbon fibers, aramid fibers, poly-imide fibers, jute fibers, nickel powder, carbon black, carbon nanotubes, graphene, lignin-derived carbon, PET fibers, PE fibers, and combinations thereof.

The polymer or combination of polymers may include polyesters, polyolefins, polyamides, polyurethanes, polyureas, poly(amide-enamine)s, polyanhydrides, polyacrylates, polyhydroxyalkanoates, poly(alkene dicarboxylate)s, silicones, thermoplastics elastomers, TPU, synthetic rubber, natural rubber, or combinations or copolymers thereof.

In some embodiments, the polymer or a combination of polymers includes polylactide. In some embodiments, the polymer or a combination of polymers includes polyhydroxyalkanoates. In some embodiments, the polymer or a combination of polymers includes aliphatic-aromatic copolyesters. In various embodiments, the polymer or a combination of polymers includes polylactide, aliphatic-aromatic copolyesters, poly(butylene adipate co-terephthalate), poly(butylene adipate), or poly(butylene succinate). In some embodiments, the polymer or a combination of polymers includes polyethylene and/or polypropylene.

The polymer or combination of polymers is bio-based, biodegradable, and/or compostable, in preferred embodiments. Because the nanocellulose is typically biodegradable and compostable, the polymer or a combination of polymers together with the nanocellulose is bio-based, biodegradable, and/or compostable, in preferred embodiments.

Some methods further include forming a hardened or finished polymer from the melt phase.

In some embodiments of such polymer blends, the nanocellulose is present in the polymer blend at a concentration of about 0.01 wt % to about 10 wt %, such as about 0.05 wt % to about 5 wt %, or about 0.1 wt % to about 2 wt %. The polymer blend may be a polymer melt or a finished polymer material, for example.

In some embodiments, the polymer or a combination of polymers includes polyesters, polyolefins, polyamides, polyurethanes, polyureas, poly(amide-enamine)s, polyanhydrides, polyacrylates, polyhydroxyalkanoates, poly(alkene dicarboxylate)s, silicones, thermoplastics Elastomers, TPU, synthetic rubber, natural rubber, or combinations or copolymers thereof. Some polymer blends include polylactide, polyhydroxyalkanoates, aliphatic-aromatic copolyesters, both polylactide and aliphatic-aromatic copolyesters, polyethylene and/or polypropylene.

Some polymer blends are bio-based, biodegradable, and/or compostable. When the nanocellulose is biodegradable and compostable, the polymer or a combination of polymers together with the hydrophobic nanocellulose is bio-based, biodegradable, and/or compostable, in preferred embodiments.

The present invention, in some variations, utilizes the discovery that nanocellulose and related materials can be produced under certain conditions including process conditions and steps associated with the AVAP® process. It has been found, surprisingly, that very high crystallinity can be produced and maintained during formation of nanofibers or nanocrystals, without the need for an enzymatic or separate acid treatment step to hydrolyze amorphous cellulose. High crystallinity can translate to mechanically strong fibers or good physical reinforcing properties, which are advantageous for composites, reinforced polymers, and high-strength spun fibers and textiles, for example.

A significant techno-economic barrier for production of cellulose nanofibrils (CNF) is high energy consumption and high cost. Using sulfur dioxide ($SO_2$) and ethanol (or other solvent), the pretreatment disclosed herein effectively removes not only hemicelluloses and lignin from biomass but also the amorphous regions of cellulose, giving a unique, highly crystalline cellulose product that requires minimal mechanical energy for conversion to CNF. The low mechanical energy requirement results from the fibrillated cellulose network formed during chemical pretreatment upon removal of the amorphous regions of cellulose.

Cellulose nanofibrils (CNF) and cellulose nanocrystals (CNC) are commonly isolated from pulp by a combination of mechanical and chemical processes. The sulfuric acid treatment used in these processes both causes an increase in the cost of the process and resulted in products with low temperature resistivity. According to the processes disclosed herein, CNFs and CNCs may be generated without the reactive sulfate groups on their surface resulting in enhanced temperature resistivity and higher degradation temperatures (~300° C. vs. ~200° C. with conventional processes). Therefore, this process can produce nanocellulose fibrils and crystals which can be incorporated into high-temperature polymers and processed at elevated temperatures. For polymers with processing temperatures above 200° C., this process opens up a new window of opportunities for use of nanocellulose-reinforced polymers. Also, the ability to produce lignin-coated (i.e., hydrophobic surface) nanocellulose fibrils and crystals will promote the dispersion of nanocellulose in many polymer precursors which are hydrophobic in nature. With careful control of the processing parameters and formulations used, the technology can be optimized for printing parts.

As intended herein, "nanocellulose" is broadly defined to include a range of cellulosic materials, including but not limited to microfibrillated cellulose, nanofibrillated cellulose, microcrystalline cellulose, nanocrystalline cellulose, and particulated or fibrillated dissolving pulp. Typically, nanocellulose as provided herein will include particles having at least one length dimension (e.g., diameter) on the nanometer scale.

"Nanofibrillated cellulose" or equivalently "cellulose nanofibrils" means cellulose fibers or regions that contain nanometer-sized particles or fibers, or both micron-sized and nanometer-sized particles or fibers. "Nanocrystalline cellulose" or equivalently "cellulose nanocrystals" means cellulose particles, regions, or crystals that contain nanometer-sized domains, or both micron-sized and nanometer-sized domains. "Micron-sized" includes from 1 µm to 100 µm and "nanometer-sized" includes from 0.01 nm to 1000 nm (1 µm). Larger domains (including long fibers) may also be present in these materials.

Certain exemplary embodiments of the invention will now be described. These embodiments are not intended to limit the scope of the invention as claimed. The order of steps may be varied, some steps may be omitted, and/or other steps may be added. Reference herein to first step, second step, etc. is for purposes of illustrating some embodiments only.

In some variations, the invention provides a polymer-nanocellulose-lignin composite comprising a hydrophobic polymer, about 0.05 wt % to about 50 wt % nanocellulose, and about 0.01 wt % to about 20 wt % lignin, wherein at least a portion of the lignin forms an interface between the hydrophobic polymer and the nanocellulose.

In some variations, the invention provides a polymer-nanocellulose-lignin composite comprising a hydrophobic polymer, about 0.01 wt % to about 20 wt % nanocellulose, and about 0.001 wt % to about 5 wt % lignin, wherein at least a portion of the lignin forms an interface between the hydrophobic polymer and the nanocellulose.

In some variations, the invention provides a polymer-nanocellulose-lignin composite comprising a hydrophobic polymer, about 0.01 wt % to more nanocellulose, and lignin, wherein at least a portion of the lignin forms an interface between the hydrophobic polymer and the nanocellulose.

In some embodiments, the composite comprises about 0.1 wt % to about 5 wt % nanocellulose or about 5 wt % to about 20 wt % nanocellulose. In some embodiments, the composite comprises about 0.1 wt % to about 10 wt % lignin. The lignin in the composite may include lignin that is chemically bonded to the nanocellulose and/or lignin that is physically deposited on the nanocellulose. The lignin may include sulfonated lignin. For example, the lignin sulfur content may be about 0.1 wt % to about 10 wt % of total lignin present in the composite (i.e., lignin basis).

The nanocellulose in the composite may include lignin-coated cellulose nanofibrils, lignin-coated cellulose nanocrystals, or a blend of lignin-coated cellulose nanofibrils and lignin-coated cellulose nanocrystals. In some embodiments, at least a portion of the nanocellulose is fully encapsulated with lignin.

In some embodiments, the polymer and at least a portion of the lignin are physically entangled at the interface. At the interface in some composites, the lignin that is physically entangled is chemically bonded lignin with the nanocellulose. In these or other composites, at the interface, the lignin that is physically entangled is physically deposited lignin on the nanocellulose. In certain composites, at the interface, the lignin that is physically entangled is a mixture of chemically bonded and physically deposited lignin on the nanocellulose.

The polymer-nanocellulose-lignin composite further comprises one or more additives selected from the group consisting of compatibilizers, plasticizers, fillers, antioxidants, colorants, flame retardants, and combinations thereof, in various embodiments. The composite may include one or more additives selected from the group consisting of carbon black, carbon nanotubes, carbon fibers, graphene, glass fibers, mica, talc, nickel powder, silica, calcium carbonate, wollastonite, stearates, and combinations thereof.

The composite may be in the form of a blend, masterbatch, pellet, extrusion feed, molding feed, extruded part, injection-molded part, blow-molded part, spun fiber, layered sheet, film, foam, container, bag, engineered part, 3D-printing substrate, 3D-printed part, or a combination thereof.

In some polymer-nanocellulose-lignin composites provided herein, the composite has higher tensile modulus compared to the polymer alone. For example, the composite may be characterized by at least an order of magnitude higher tensile modulus compared to the polymer.

The present invention also provides a process for producing a nanocellulose-polymer composite material, the process comprising:
(a) providing a lignocellulosic biomass feedstock;
(b) fractionating the feedstock in the presence of an acid, a solvent for lignin, and water, to generate cellulose-rich solids and a liquid containing hemicellulose and lignin, wherein at least a portion of the lignin deposits onto a surface of, or within fiber pores of, the cellulose-rich solids, thereby rendering the cellulose-rich solids at least partially hydrophobic;
(c) mechanically treating the cellulose-rich solids to form a hydrophobic lignin-coated nanocellulose material comprising cellulose fibrils and/or cellulose crystals;
(d) hydrolyzing the hemicellulose to generate fermentable hemicellulosic sugars;
(e) fermenting the fermentable hemicellulosic sugars with a suitable microorganism to generate a monomer or monomer precursor;
(f) polymerizing the monomer or a derivative of the monomer or monomer precursor to produce a polymer; and
(g) combining the polymer with the lignin-coated nanocellulose to generate a polymer-nanocellulose-lignin composite material.

The acid may be selected from the group consisting of organic acids, inorganic acids, ionic liquid acid functional groups, and combinations thereof. In certain preferred embodiments, the acid is selected from the group consisting of sulfur dioxide, sulfurous acid, sulfuric acid, lignosulfonic acid, and combinations thereof. The solvent may be selected from the group consisting of alkanes, olefins, aromatics, alcohols, diols, organic acids, organic acid esters, ketones, aldehydes, and combinations thereof.

In some embodiments, the liquid from step (b) further contains glucose, which is optionally fermented to an additional amount of the monomer or monomer precursor.

The monomer may be an organic acid (such as lactic acid) or a derivative thereof (such as lactide). When step (e) generates a monomer precursor, it may be ethanol, for example, which in converted to olefins (e.g., ethylene) for producing a polymer (e.g., polyethylene) in step (f), prior to combining with the lignin-coated nanocellulose to generate a polymer-nanocellulose-lignin composite material The disclosed processes may produce a polymer-nanocellulose-lignin composite material that is substantially or even entirely derived from biomass. In some embodiments of the invention, a polymer-nanocellulose-lignin composite material has 100% renewable carbon content.

Various industrial and consumer products may be fabricated from the polymer-nanocellulose-lignin composite material. These include any known products containing polymers, as well as new products (such as engineered composites).

Polymers that may be included in the polymer-nanocellulose-lignin composite material may be hydrophobic, partially hydrophobic, or oleophilic, for example. Hydrophilic polymers may be modified to render them at least partially hydrophobic, with suitable coatings or combinations of components (e.g., interpenetrating networks of polymers).

Polymers herein may be selected from polyesters, polyolefins, polyamides, polyurethanes, polyureas, poly(amide-enamine)s, polyanhydrides, polyacrylates, polyhydroxyalkanoates, poly(alkene dicarboxylate)s, silicones, and combinations or copolymers (e.g., aliphatic-aromatic copolyesters) thereof.

In various embodiments, a polymer is selected from the group consisting of polyethylene, polypropylene, polybutene, polyisobutylene, polybutadiene, polyisoprene, poly (ethylene-co-acrylic acid), poly(lactic acid) (or polylactide), poly(glycolic acid) (or polyglycolide), poly(hydroxybutyrate), poly(butylene adipate-co-terephtalate), poly(butylene succinate), poly(hydroxybutyrate-co-hydroxyvalerate), poly(ethylene terephthalate), polyvinyl alcohol, polystyrene, poly(butyl acrylate), poly(tert-butyl acrylate-co-ethyl acrylate-co-methacrylic acid), poly(ethyl acrylate), poly(2-ethylhexyl acrylate), poly(methyl acrylate), polyacrylonitrile, poly(acrylonitrile-co-methyl acrylate), poly(styrene-co-maleic anhydride), poly(methyl methacrylate), poly(alkyl methacrylate), polyvinylcyclohexane, poly(Bisphenol A carbonate), poly(propylene carbonate), poly(1,4-butylene adipate), poly(1,4-butylene succinate), poly(1,4-butylene terephthalate), poly(ethylene succinate), poly(vinyl acetate), poly(propylene glycol), poly(tetrahydrofuran), poly(ethyl vinyl ether), polydimethylsiloxane, nylons (aliphatic polyamides), and combinations or copolymers thereof. Carbonaceous polymers may also be incorporated in the composites. Examples of carbonaceous polymers include polyacenaphthylene, graphite, graphene, and carbon fibers.

In some embodiments, the polymer is or includes a biodegradable polymer, such as any polymer described in Vroman and Tighzert, "Biodegradable Polymers," *Materials* 2009, 2, 307-344, which is hereby incorporated by reference herein.

Polymers or copolymers may be produced by polymerizing one or more monomers selected from the group consisting of acrylics, amides, carbon, carbonates, dienes, esters, ethers, fluorocarbons, imides, olefins, organic acids (e.g., lactic acid, glycolic acid, succinic acid, hydroxypropionic acid, etc.), styrenes, siloxanes, vinyl acetals, vinyl and vinylidene chlorides, vinyl esters, vinyl ethers, vinyl ketones, vinylpyridine, vinypyrrolidone, and combinations thereof.

Polylactide is an exemplary polymer for the purposes of this disclosure and detailed description, but the invention is expressly not limited in any way to polylactide.

In some variations, the invention provides a polylactide-nanocellulose-lignin composite comprising polylactide, about 0.05 wt % to about 30 wt % nanocellulose, and about 2 wt % to about 20 wt % lignin, wherein at least a portion of the lignin forms a hydrophobic interface between the polylactide and the nanocellulose. In some embodiments, the composite comprises about 0.1 wt % to about 5 wt % nanocellulose. In other embodiments, the composite comprises about 5 wt % to about 20 wt % nanocellulose.

In some embodiments, the composite comprises about 3 wt % to about 10 wt % lignin. The lignin may be chemically bonded to the nanocellulose and/or physically deposited on the nanocellulose. In some embodiments, the lignin includes sulfonated lignin. For example, the sulfur content may be about 0.1 wt % to about 10 wt % of total lignin present in the composite.

In some polylactide-nanocellulose-lignin composites, the nanocellulose comprises lignin-coated cellulose nanofibrils. In these or other polylactide-nanocellulose-lignin composites, the nanocellulose comprises lignin-coated cellulose nanocrystals. In some embodiments, the nanocellulose comprises a blend of lignin-coated cellulose nanofibrils and lignin-coated cellulose nanocrystals. In certain embodiments, at least a portion of the nanocellulose is lignin-encapsulated nanocellulose. In any of these embodiments, some of the lignin may be lignin that does not coat, chemically bond with, or physically attach to nanocellulose (i.e. there can be bulk, dispersed lignin particles present).

In some embodiments, the polylactide and at least a portion of the lignin are physically entangled at the interface. At the interface, the lignin that is physically entangled may be chemically bonded lignin and/or physically deposited lignin on/with the nanocellulose. In certain embodiments, at the interface, the lignin that is physically entangled is a mixture of chemically bonded and physically deposited lignin on the nanocellulose.

In various embodiments, the polylactide-nanocellulose-lignin composite further comprises one or more additives selected from the group consisting of compatibilizers, plasticizers, fillers, antioxidants, colorants, flame retardants, and combinations thereof. For example, the composite may contain one or more additives selected from the group consisting of carbon black, carbon nanotubes, carbon fibers, graphene, glass fibers, mica, talc, nickel powder, silica, calcium carbonate, wollastonite, stearates, and combinations thereof.

Jacobsen et al., "Plasticizing polylactide—the effect of different plasticizers on the mechanical properties," *Polymer Engineering &Science*, Volume 39, Issue 7, pages 1303-1310, July 1999, is hereby incorporated by reference herein for its teachings of various plasticizers that may be incorporated in compositions or composites herein.

In various embodiments, the polylactide-nanocellulose-lignin composite is in the form of a blend, masterbatch, pellet, extrusion feed, molding feed, extruded part, injection-molded part, blow-molded part, spun fiber, layered sheet, film, foam, container, bag, engineered part, 3D-printing substrate, 3D-printed part, or a combination thereof.

The presence of lignin in the composite, at the interface between polylactide and nanocellulose, enables a well-dispersed material with improved properties (including strength and barrier properties), compared to a polylactide-nanocellulose composite (without any lignin) or compared to polylactide alone.

The polylactide-nanocellulose-lignin composite provided in some embodiments has higher tensile modulus compared to polylactide—such as about 1, 2, 3, 4 or more orders of magnitude higher in tensile modulus compared to polylactide alone.

The polylactide-nanocellulose-lignin composite provided in some embodiments has lower vapor (e.g., oxygen, $CO_2$, or water vapor) permeability compared to polylactide.

The polylactide-nanocellulose-lignin composite provided in some embodiments has better heat stability (such as heat-distortion temperature) compared to polylactide.

The invention, in some variations, also provides a process for producing a nanocellulose-polylactide composite material, the process comprising:
(a) providing a lignocellulosic biomass feedstock;
(b) fractionating the feedstock in the presence of an acid, a solvent for lignin, and water, to generate cellulose-rich solids and a liquid containing hemicellulose and lignin, wherein at least a portion of the lignin deposits onto a surface of, or within fiber pores of, the cellulose-rich solids, thereby rendering the cellulose-rich solids at least partially hydrophobic;
(c) mechanically treating the cellulose-rich solids to form a hydrophobic lignin-coated nanocellulose material comprising cellulose fibrils and/or cellulose crystals;
(d) hydrolyzing the hemicellulose to generate fermentable hemicellulosic sugars;
(e) fermenting the fermentable hemicellulosic sugars with a suitable lactic acid microorganism to generate lactic acid;
(f) polymerizing the lactic acid, or an oligomer or lactide thereof, to polylactide; and
(g) combining the polylactide with the lignin-coated nanocellulose to generate a polylactide-nanocellulose-lignin composite material.

The acid may be selected from the group consisting of organic acids, inorganic acids, ionic liquid acid functional groups, and combinations thereof. For example, the acid may be selected from the group consisting of sulfur dioxide, sulfurous acid, sulfuric acid, lignosulfonic acid, and combinations thereof.

The solvent may be selected from the group consisting of alkanes, olefins, aromatics, alcohols, diols, organic acids, organic acid esters, ketones, aldehydes, and combinations thereof.

In some embodiments, the liquid from step (b) further contains glucose, which may be fermented to additional lactic acid. Such lactic acid may include L-lactic acid, D-lactic acid, or a combination of L-lactic acid and D-lactic acid, which when polymerized (typically via lactide) will produce polylactide comprising L-polylactide, D-polylactide, meso-polylactide, L,D-polylactide, or combinations thereof.

The disclosed processes may produce a polylactide-nanocellulose-lignin composite material that is substantially or even entirely derived from biomass. In some embodiments of the invention, a polylactide-nanocellulose-lignin composite material has 100% renewable carbon content.

Various industrial and consumer products may be fabricated from the polylactide-nanocellulose-lignin composite material. These include any known products containing polylactide (see e.g. www.natureworksllc.com/Product-and-Applications), as well as new products (such as engineered composites).

Some variations are premised on the realization that all components of hydrophobic nanocellulose-polylactide composite materials may be produced from a single biomass source. The main components of biomass are cellulose, hemicellulose, and lignin. The cellulose can be converted to nanocellulose using the processes described in detail herein. The lignin can be deposited onto the nanocellulose to increase its hydrophobicity. Finally, the hemicelluloses can be converted to monomer sugars and then fermented to lactic acid, using known organisms, followed by polymerization of lactic acid (such as via lactide) to polylactide. The polylactide may then be formed into a nanocellulose-polylactide composite.

In some variations, the present invention provides a process for producing a nanocellulose-polylactide composite material, the process comprising:
(a) providing a lignocellulosic biomass feedstock;
(b) fractionating the feedstock in the presence of an acid, a solvent for lignin, and water, to generate cellulose-rich solids and a liquid containing hemicellulose and lignin, wherein at least a portion of the lignin deposits onto a surface of the cellulose-rich solids, thereby rendering the cellulose-rich solids at least partially hydrophobic;
(c) mechanically treating the cellulose-rich solids to form a hydrophobic nanocellulose material comprising cellulose fibrils and/or cellulose crystals;
(d) hydrolyzing the hemicellulose to generate fermentable hemicellulosic sugars;
(e) fermenting the fermentable hemicellulosic sugars with a suitable lactic acid microorganism to generate lactic acid;
(f) polymerizing the lactic acid, or an oligomer or lactide thereof, to polylactide; and
(g) combining the polylactide with the nanocellulose to generate a nanocellulose-polylactide composite material.

In some embodiments, the acid is selected from the group consisting of organic acids, inorganic acids, ionic liquid acid functional groups, and combinations thereof. For example, the acid may be selected from the group consisting of sulfur dioxide, sulfurous acid, sulfuric acid, lignosulfonic acid, and combinations thereof.

In some embodiments, the solvent is selected from the group consisting of alkanes, olefins, aromatics, alcohols, diols, organic acids, organic acid esters, ketones, aldehydes, and combinations thereof.

The lactic acid produced may be L-lactic acid, D-lactic acid, or a combination of L-lactic acid and D-lactic acid. In some embodiments, the liquid from step (b) further contains glucose, which is optionally fermented to additional lactic acid (which may be L and/or D isomers). Fermentation of hemicellulose sugars, including (but not limited to) glucose and xylose, is known in the art using genetically modified yeasts or bacteria.

The polylactide may include L-polylactide, D-polylactide, meso-polylactide, L,D-polylactide, or combinations thereof. Polymerization of lactic acid, lactic acid oligomers, or lactide (a cyclic dimer of lactic acid) is well-known in the industry (see, for example, www.natureworksllc.com/Technical-Resources).

In some variations, a nanocellulose-polylactide composite material are provided. In some embodiments, a nanocellulose-polylactide composite material is produced by a process comprising:
(a) providing a lignocellulosic biomass feedstock;
(b) fractionating the feedstock in the presence of an acid, a solvent for lignin, and water, to generate cellulose-rich solids and a liquid containing hemicellulose and lignin, optionally wherein at least a portion of the lignin is allowed to deposit onto a surface of the cellulose-rich solids, thereby rendering the cellulose-rich solids at least partially hydrophobic;
(c) mechanically treating the cellulose-rich solids to form a hydrophobic nanocellulose material comprising cellulose fibrils and/or cellulose crystals;
(d) hydrolyzing the hemicellulose to generate fermentable hemicellulosic sugars;
(e) fermenting the fermentable hemicellulosic sugars with a suitable lactic acid microorganism to generate lactic acid;
(f) polymerizing the lactic acid, or an oligomer or lactide thereof, to polylactide; and
(g) combining the polylactide with the nanocellulose to generate a nanocellulose-polylactide composite material.

The nanocellulose-polylactide composite material is preferably entirely derived from biomass. The nanocellulose-polylactide composite material comprises 100% renewable carbon content, in some embodiments.

Certain embodiments provide a multilayered nanocellulose-lignin-polylactide composite material comprising a lignin layer disposed on a nanocellulose layer, and a polylactide layer disposed on the lignin layer.

In some embodiments, a product comprising the nanocellulose-polylactide composite material is provided. Many types of products are possible, including films, coatings, packaging, utensils, fibers, fabrics, apparel, durable goods, nonwovens, and so on.

In some variations, a process for producing a nanocellulose material comprises:
(a) providing a lignocellulosic biomass feedstock;
(b) fractionating the feedstock in the presence of an acid, a solvent for lignin, and water, to generate cellulose-rich solids and a liquid containing hemicellulose and lignin;
(c) mechanically treating the cellulose-rich solids to form cellulose fibrils and/or cellulose crystals, thereby generating a nanocellulose material having a crystallinity (i.e., cellulose crystallinity) of at least 60%; and
(d) recovering the nanocellulose material.

In some embodiments, the acid is selected from the group consisting of sulfur dioxide, sulfurous acid, sulfur trioxide, sulfuric acid, lignosulfonic acid, and combinations thereof. In particular embodiments, the acid is sulfur dioxide.

The biomass feedstock may be selected from hardwoods, softwoods, forest residues, eucalyptus, industrial wastes, pulp and paper wastes, consumer wastes, or combinations thereof. Some embodiments utilize agricultural residues, which include lignocellulosic biomass associated with food crops, annual grasses, energy crops, or other annually renewable feedstocks. Exemplary agricultural residues include, but are not limited to, corn stover, corn fiber, wheat straw, sugarcane bagasse, sugarcane straw, rice straw, oat straw, barley straw, miscanthus, energy cane straw/residue, or combinations thereof. The process disclosed herein benefits from feedstock flexibility; it is effective for a wide variety of cellulose-containing feedstocks.

As used herein, "lignocellulosic biomass" means any material containing cellulose and lignin. Lignocellulosic biomass may also contain hemicellulose. Mixtures of one or more types of biomass can be used. In some embodiments, the biomass feedstock comprises both a lignocellulosic component (such as one described above) in addition to a sucrose-containing component (e.g., sugarcane or energy cane) and/or a starch component (e.g., corn, wheat, rice, etc.). Various moisture levels may be associated with the starting biomass. The biomass feedstock need not be, but may be, relatively dry. In general, the biomass is in the form of a particulate or chip, but particle size is not critical in this invention.

In some embodiments, during step (c), the cellulose-rich solids are treated with a total mechanical energy of less than about 1000 kilowatt-hours per ton of the cellulose-rich solids, such as less than about 950, 900, 850, 800, 750, 700, 650, 600, 550, 500, 450, 400, 350, 300, or 250 kilowatt-hours per ton of the cellulose-rich solids. In certain embodiments, the total mechanical energy is from about 100 kilowatt-hours to about 400 kilowatt-hours per ton of the cellulose-rich solids. Energy consumption may be measured in any other suitable units. An ammeter measuring current drawn by a motor driving the mechanical treatment device is one way to obtain an estimate of the total mechanical energy.

Mechanically treating in step (c) may employ one or more known techniques such as, but by no means limited to, milling, grinding, beating, sonicating, or any other means to form or release nanofibrils and/or nanocrystals in the cellulose. Essentially, any type of mill or device that physically separates fibers may be utilized. Such mills are well-known in the industry and include, without limitation, Valley beaters, single disk refiners, double disk refiners, conical refiners, including both wide angle and narrow angle, cylindrical refiners, homogenizers, microfluidizers, and other similar milling or grinding apparatus. See, for example, Smook, *Handbook for Pulp &Paper Technologists*, Tappi Press, 1992; and Hubbe et al., "Cellulose Nanocomposites: A Review," *BioResources* 3(3), 929-980 (2008).

The extent of mechanical treatment may be monitored during the process by any of several means. Certain optical instruments can provide continuous data relating to the fiber length distributions and % fines, either of which may be used to define endpoints for the mechanical treatment step. The time, temperature, and pressure may vary during mechanical treatment. For example, in some embodiments, sonication for a time from about 5 minutes to 2 hours, at ambient temperature and pressure, may be utilized.

In some embodiments, a portion of the cellulose-rich solids is converted to nanofibrils while the remainder of the cellulose-rich solids is not fibrillated. In various embodiments, about 10%, 20%, 30%, 40%, 50%, 60%, 70%, 80%, 90%, 95%, 99%, or substantially all of the cellulose-rich solids are fibrillated into nanofibrils.

In some embodiments, a portion of the nanofibrils is converted to nanocrystals while the remainder of the nanofibrils is not converted to nanocrystals. In various embodiments, about 10%, 20%, 30%, 40%, 50%, 60%, 70%, 80%, 90%, 95%, 99%, or substantially all of the nanofibrils is converted to nanocrystals. During drying, it is possible for a small amount of nanocrystals to come back together and form nanofibrils.

Following mechanical treatment, the nanocellulose material may be classified by particle size. A portion of material may be subjected to a separate process, such as enzymatic hydrolysis to produce glucose. Such material may have good crystallinity, for example, but may not have desirable particle size or degree of polymerization.

Step (c) may further comprise treatment of the cellulose-rich solids with one or more enzymes or with one or more acids. When acids are employed, they may be selected from the group consisting of sulfur dioxide, sulfurous acid, lignosulfonic acid, acetic acid, formic acid, and combinations thereof. Acids associated with hemicellulose, such as acetic acid or uronic acids, may be employed, alone or in conjunction with other acids. Also, step (c) may include treatment of the cellulose-rich solids with heat. In some embodiments, step (c) does not employ any enzymes or acids.

In step (c), when an acid is employed, the acid may be a strong acid such as sulfuric acid, nitric acid, or phosphoric acid, for example. Weaker acids may be employed, under more severe temperature and/or time. Enzymes that hydrolyze cellulose (i.e., cellulases) and possibly hemicellulose (i.e., with hemicellulase activity) may be employed in step (c), either instead of acids, or potentially in a sequential configuration before or after acidic hydrolysis.

In some embodiments, the process comprises enzymatically treating the cellulose-rich solids to hydrolyze amorphous cellulose. In other embodiments, or sequentially prior to or after enzymatic treatment, the process may comprise acid-treating the cellulose-rich solids to hydrolyze amorphous cellulose.

In some embodiments, the process further comprises enzymatically treating the nanocrystalline cellulose. In other embodiments, or sequentially prior to or after enzymatic treatment, the process further comprises acid-treating treating the nanocrystalline cellulose.

If desired, an enzymatic treatment may be employed prior to, or possibly simultaneously with, the mechanical treatment. However, in preferred embodiments, no enzyme treatment is necessary to hydrolyze amorphous cellulose or weaken the structure of the fiber walls before isolation of nanofibers.

Following mechanical treatment, the nanocellulose may be recovered. Separation of cellulose nanofibrils and/or nanocrystals may be accomplished using apparatus capable of disintegrating the ultrastructure of the cell wall while preserving the integrity of the nanofibrils. For example, a homogenizer may be employed. In some embodiments, cellulose aggregate fibrils are recovered, having component fibrils in range of 1-100 nm width, wherein the fibrils have not been completely separated from each other.

The process may further comprise bleaching the cellulose-rich solids prior to step (c) and/or as part of step (c). Alternatively, or additionally, the process may further comprise bleaching the nanocellulose material during step (c) and/or following step (c). Any known bleaching technology or sequence may be employed, including enzymatic bleaching.

The nanocellulose material may include, or consist essentially of, nanofibrillated cellulose. The nanocellulose material may include, or consist essentially of, nanocrystalline cellulose. In some embodiments, the nanocellulose material may include, or consist essentially of, nanofibrillated cellulose and nanocrystalline cellulose.

In some embodiments, the crystallinity of the cellulose-rich solids (i.e., the nanocellulose precursor material) is at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86% or higher. In these or other embodiments, the crystallinity of the nanocellulose material is at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86% or higher. The crystallinity may be measured using any known techniques. For example, X-ray diffraction and solid-state $^{13}C$ nuclear magnetic resonance may be utilized.

It is remarkable that the nanocellulose precursor material has high crystallinity—which generally contributes to mechanical strength-yet, very low mechanical energy consumption is necessary to break apart the nanocellulose precursor material into nanofibrils and nanocrystals. It is believed that since the mechanical energy input is low, the high crystallinity is essentially maintained in the final product.

In some embodiments, the nanocellulose material is characterized by an average degree of polymerization from about 100 to about 1500, such as about 125, 150, 175, 200, 225, 250, 300, 400, 500, 600, 700, 800, 900, 1000, 1100, 1200, 1300, or 1400. For example, the nanocellulose material may be characterized by an average degree of polymerization from about 300 to about 700, or from about 150 to about 250. The nanocellulose material, when in the form of nanocrystals, may have a degree of polymerization less than 100, such as about 75, 50, 25, or 10. Portions of the material may have a degree of polymerization that is higher than 1500, such as about 2000, 3000, 4000, or 5000.

In some embodiments, the nanocellulose material is characterized by a degree of polymerization distribution having a single peak. In other embodiments, the nanocellulose material is characterized by a degree of polymerization distribution having two peaks, such as one centered in the range of 150-250 and another peak centered in the range of 300-700.

In some embodiments, the nanocellulose material is characterized by an average length-to-width aspect ratio of particles from about 10 to about 1000, such as about 15, 20, 25, 35, 50, 75, 100, 150, 200, 250, 300, 400, or 500. Nanofibrils are generally associated with higher aspect ratios than nanocrystals. Nanocrystals, for example, may have a length range of about 100 nm to 500 nm and a diameter of about 4 nm, translating to an aspect ratio of 25 to 125. Nanofibrils may have a length of about 2000 nm and diameter range of 5 to 50 nm, translating to an aspect ratio of 40 to 400. In some embodiments, the aspect ratio is less than 50, less than 45, less than 40, less than 35, less than 30, less than 25, less than 20, less than 15, or less than 10.

Optionally, the process further comprises hydrolyzing amorphous cellulose into glucose in step (b) and/or step (c), recovering the glucose, and fermenting the glucose to a fermentation product. Optionally, the process further comprises recovering, fermenting, or further treating hemicellulosic sugars derived from the hemicellulose. Optionally, the process further comprises recovering, combusting, or further treating the lignin.

Glucose that is generated from hydrolysis of amorphous cellulose may be integrated into an overall process to produce ethanol, or another fermentation co-product. Thus in some embodiments, the process further comprises hydrolyzing amorphous cellulose into glucose in step (b) and/or step (c), and recovering the glucose. The glucose may be purified and sold. Or the glucose may be fermented to a fermentation product, such as but not limited to ethanol. The glucose or a fermentation product may be recycled to the front end, such as to hemicellulose sugar processing, if desired.

When hemicellulosic sugars are recovered and fermented, they may be fermented to produce a monomer or precursor thereof. The monomer may be polymerized to produce a polymer, which may then be combined with the nanocellulose material to form a polymer-nanocellulose composite.

In some embodiments, the nanocellulose material is at least partially hydrophobic via deposition of at least some of the lignin onto a surface of the cellulose-rich solids during step (b). In these or other embodiments, the nanocellulose material is at least partially hydrophobic via deposition of at least some of the lignin onto a surface of the nanocellulose material during step (c) or step (d).

In some embodiments, the process further comprises chemically converting the nanocellulose material to one or more nanocellulose derivatives. For example, nanocellulose derivatives may be selected from the group consisting of nanocellulose esters, nanocellulose ethers, nanocellulose ether esters, alkylated nanocellulose compounds, cross-linked nanocellulose compounds, acid-functionalized nanocellulose compounds, base-functionalized nanocellulose compounds, and combinations thereof.

Various types of nanocellulose functionalization or derivatization may be employed, such as functionalization using polymers, chemical surface modification, functionalization using nanoparticles (i.e. other nanoparticles besides the nanocellulose), modification with inorganics or surfactants, or biochemical modification.

Certain variations provide a process for producing a nanocellulose material, the process comprising:
 (a) providing a lignocellulosic biomass feedstock;
 (b) fractionating the feedstock in the presence of sulfur dioxide, a solvent for lignin, and water, to generate cellulose-rich solids and a liquid containing hemicellulose oligomers and lignin, wherein the crystallinity of the cellulose-rich solids is at least 70%, wherein $SO_2$ concentration is from about 10 wt % to about 50 wt %, fractionation temperature is from about 130° C. to about 200° C., and fractionation time is from about 30 minutes to about 4 hours;
 (c) mechanically treating the cellulose-rich solids to form cellulose fibrils and/or cellulose crystals, thereby generating a nanocellulose material having a crystallinity of at least 70%; and
 (d) recovering the nanocellulose material.

In some embodiments, the $SO_2$ concentration is from about 12 wt % to about 30 wt %. In some embodiments, the fractionation temperature is from about 140° C. to about 170° C. In some embodiments, the fractionation time is from about 1 hour to about 2 hours. The process may be controlled such that during step (b), a portion of the solubilized lignin intentionally deposits back onto a surface of the cellulose-rich solids, thereby rendering the cellulose-rich solids at least partially hydrophobic.

A significant factor limiting the application of strength-enhancing, lightweight nanocellulose in composites is cellulose's inherent hydrophilicity. Surface modification of the nanocellulose surface to impart hydrophobicity to enable uniform dispersion in a hydrophobic polymer matrix is an active area of study. It has been discovered that when preparing nanocellulose using the processes described herein, lignin may condense on pulp under certain conditions, giving a rise in Kappa number and production of a brown or black material. The lignin increases the hydrophobicity of the nanocellulose precursor material, and that hydrophobicity is retained during mechanical treatment provided that there is not removal of the lignin through bleaching or other steps. (Some bleaching may still be performed, either to adjust lignin content or to attack a certain type of lignin, for example.)

In some embodiments, the present invention provides a process for producing a hydrophobic nanocellulose material, the process comprising:

(a) providing a lignocellulosic biomass feedstock;
(b) fractionating the feedstock in the presence of an acid, a solvent for lignin, and water, to generate cellulose-rich solids and a liquid containing hemicellulose and lignin, wherein a portion of the lignin deposits onto a surface of the cellulose-rich solids, thereby rendering the cellulose-rich solids at least partially hydrophobic;
(c) mechanically treating the cellulose-rich solids to form cellulose fibrils and/or cellulose crystals, thereby generating a hydrophobic nanocellulose material having a crystallinity of at least 60%; and
(d) recovering the hydrophobic nanocellulose material.

In some embodiments, the acid is selected from the group consisting of sulfur dioxide, sulfurous acid, sulfur trioxide, sulfuric acid, lignosulfonic acid, and combinations thereof.

In some embodiments, during step (c), the cellulose-rich solids are treated with a total mechanical energy of less than about 1000 kilowatt-hours per ton of the cellulose-rich solids, such as less than about 500 kilowatt-hours per ton of the cellulose-rich solids.

The crystallinity of the nanocellulose material is at least 70% or at least 80%, in various embodiments.

The nanocellulose material may include nanofibrillated cellulose, nanocrystalline cellulose, or both nanofibrillated and nanocrystalline cellulose. The nanocellulose material may be characterized by an average degree of polymerization from about 100 to about 1500, such as from about 300 to about 700, or from about 150 to about 250, for example (without limitation).

Step (b) may include process conditions, such as extended time and/or temperature, or reduced concentration of solvent for lignin, which tend to promote lignin deposition onto fibers. Alternatively, or additionally, step (b) may include one or more washing steps that are adapted to deposit at least some of the lignin that was solubilized during the initial fractionation. One approach is to wash with water rather than a solution of water and solvent. Because lignin is generally not soluble in water, it will begin to precipitate. Optionally, other conditions may be varied, such as pH and temperature, during fractionation, washing, or other steps, to optimize the amount of lignin deposited on surfaces. It is noted that in order for the lignin surface concentration to be higher than the bulk concentration, the lignin needs to be first pulled into solution and then redeposited; internal lignin (within particles of nanocellulose) does not enhance hydrophobicity in the same way.

Optionally, the process for producing a hydrophobic nanocellulose material may further include chemically modifying the lignin to increase hydrophobicity of the nanocellulose material. The chemical modification of lignin may be conducted during step (b), step (c), step (d), following step (d), or some combination.

High loading rates of lignin have been achieved in thermoplastics. Even higher loading levels are obtained with well-known modifications of lignin. The preparation of useful polymeric materials containing a substantial amount of lignin has been the subject of investigations for more than thirty years. Typically, lignin may be blended into polyolefins or polyesters by extrusion up to 25-40 wt % while satisfying mechanical characteristics. In order to increase the compatibility between lignin and other hydrophobic polymers, different approaches have been used. For example, chemical modification of lignin may be accomplished through esterification with long-chain fatty acids.

Any known chemical modifications may be carried out on the lignin, to further increase the hydrophobic nature of the lignin-coated nanocellulose material provided by embodiments of this invention.

The present invention also provides, in some variations, a process for producing a nanocellulose-containing product, the process comprising:

(a) providing a lignocellulosic biomass feedstock;
(b) fractionating the feedstock in the presence of an acid, a solvent for lignin, and water, to generate cellulose-rich solids and a liquid containing hemicellulose and lignin;
(c) mechanically treating the cellulose-rich solids to form cellulose fibrils and/or cellulose crystals, thereby generating a nanocellulose material having a crystallinity of at least 60%; and
(d) incorporating at least a portion of the nanocellulose material into a nanocellulose-containing product.

The nanocellulose-containing product includes the nanocellulose material, or a treated form thereof. In some embodiments, the nanocellulose-containing product consists essentially of the nanocellulose material.

In some embodiments, step (d) comprises forming a structural object that includes the nanocellulose material, or a derivative thereof.

In some embodiments, step (d) comprises forming a foam or aerogel that includes the nanocellulose material, or a derivative thereof.

In some embodiments, step (d) comprises combining the nanocellulose material, or a derivative thereof, with one or more other materials to form a composite. For example, the other material may include a polymer selected from polyolefins, polyesters, polyurethanes, polyamides, or combinations thereof. Alternatively, or additionally, the other material may include carbon in various forms, such as graphene.

The nanocellulose material incorporated into a nanocellulose-containing product may be at least partially hydrophobic via deposition of at least some of the lignin onto a surface of the cellulose-rich solids during step (b). Also, the nanocellulose material may be at least partially hydrophobic via deposition of at least some of the lignin onto a surface of the nanocellulose material during step (c) or step (d).

In some embodiments, step (d) comprises forming a film comprising the nanocellulose material, or a derivative thereof. The film is optically transparent and flexible, in certain embodiments.

In some embodiments, step (d) comprises forming a coating or coating precursor comprising the nanocellulose material, or a derivative thereof. In some embodiments, the nanocellulose-containing product is a paper coating.

In some embodiments, the nanocellulose-containing product is configured as a catalyst, catalyst substrate, or co-catalyst. In some embodiments, the nanocellulose-containing product is configured electrochemically for carrying or storing an electrical current or voltage.

In some embodiments, the nanocellulose-containing product is incorporated into a filter, membrane, or other separation device.

In some embodiments, the nanocellulose-containing product is incorporated as an additive into a coating, paint, or adhesive. In some embodiments, the nanocellulose-containing product is incorporated as a cement additive.

In some embodiments, the nanocellulose-containing product is incorporated as a thickening agent or rheological modifier. For example, the nanocellulose-containing product may be an additive in a drilling fluid, such as (but not limited to) an oil recovery fluid and/or a gas recovery fluid.

The present invention also provides nanocellulose compositions. In some variations, a nanocellulose composition comprises nanofibrillated cellulose with a cellulose crystallinity of about 70% or greater. The nanocellulose composition may include lignin and sulfur.

The nanocellulose material may further contain some sulfonated lignin that is derived from sulfonation reactions with $SO_2$ (when used as the acid in fractionation) during the biomass digestion. The amount of sulfonated lignin may be about 0.1 wt % (or less), 0.2 wt %, 0.5 wt %, 0.8 wt %, 1 wt %, or more. Also, without being limited by any theory, it is speculated that a small amount of sulfur may chemically react with cellulose itself, in some embodiments.

In some variations, a nanocellulose composition comprises nanofibrillated cellulose and nanocrystalline cellulose, wherein the nanocellulose composition is characterized by an overall cellulose crystallinity of about 70% or greater. The nanocellulose composition may include lignin and sulfur.

In some variations, a nanocellulose composition comprises nanocrystalline cellulose with a cellulose crystallinity of about 80% or greater, wherein the nanocellulose composition comprises lignin and sulfur.

In some embodiments, the cellulose crystallinity is about 75% or greater, such as about 80% or greater, or about 85% or greater. In various embodiments, the nanocellulose composition is not derived from tunicates.

The nanocellulose composition of some embodiments is characterized by an average cellulose degree of polymerization from about 100 to about 1000, such as from about 300 to about 700 or from about 150 to about 250. In certain embodiments, the nanocellulose composition is characterized by a cellulose degree of polymerization distribution having a single peak. In certain embodiments, the nanocellulose composition is free of enzymes.

Other variations provide a hydrophobic nanocellulose composition with a cellulose crystallinity of about 70% or greater, wherein the nanocellulose composition contains nanocellulose particles having a surface concentration of lignin that is greater than a bulk (internal particle) concentration of lignin. In some embodiments, there is a coating or thin film of lignin on nanocellulose particles, but the coating or film need not be uniform.

The hydrophobic nanocellulose composition may have a cellulose crystallinity is about 75% or greater, about 80% or greater, or about 85% or greater. The hydrophobic nanocellulose composition may further include sulfur.

The hydrophobic nanocellulose composition may or may not be derived from tunicates. The hydrophobic nanocellulose composition may be free of enzymes.

In some embodiments, the hydrophobic nanocellulose composition is characterized by an average cellulose degree of polymerization from about 100 to about 1500, such as from about 300 to about 700 or from about 150 to about 250. The nanocellulose composition may be characterized by a cellulose degree of polymerization distribution having a single peak.

A nanocellulose-containing product may include any of the disclosed nanocellulose compositions. Many nanocellulose-containing products are possible. For example, a nanocellulose-containing product may be selected from the group consisting of a structural object, a foam, an aerogel, a polymer composite, a carbon composite, a film, a coating, a coating precursor, a current or voltage carrier, a filter, a membrane, a catalyst, a catalyst substrate, a coating additive, a paint additive, an adhesive additive, a cement additive, a paper coating, a thickening agent, a rheological modifier, an additive for a drilling fluid, and combinations or derivatives thereof.

Some variations provide a nanocellulose material produced by a process comprising:
(a) providing a lignocellulosic biomass feedstock;
(b) fractionating the feedstock in the presence of an acid, a solvent for lignin, and water, to generate cellulose-rich solids and a liquid containing hemicellulose and lignin;
(c) mechanically treating the cellulose-rich solids to form cellulose fibrils and/or cellulose crystals, thereby generating a nanocellulose material having a crystallinity of at least 60%; and
(d) recovering the nanocellulose material.

Some embodiments provide a polymer-nanocellulose composite material produced by a process comprising:
(a) providing a lignocellulosic biomass feedstock;
(b) fractionating the feedstock in the presence of an acid, a solvent for lignin, and water, to generate cellulose-rich solids and a liquid containing hemicellulose and lignin;
(c) mechanically treating the cellulose-rich solids to form cellulose fibrils and/or cellulose crystals, thereby generating a nanocellulose material having a crystallinity of at least 60%;
(d) recovering the nanocellulose material;
(e) fermenting hemicellulosic sugars derived from the hemicellulose to produce a monomer or precursor thereof;
(f) polymerizing the monomer to produce a polymer; and
(g) combining the polymer and the nanocellulose material to form the polymer-nanocellulose composite.

Some variations provide a nanocellulose material produced by a process comprising:
(a) providing a lignocellulosic biomass feedstock;
(b) fractionating the feedstock in the presence of sulfur dioxide, a solvent for lignin, and water, to generate cellulose-rich solids and a liquid containing hemicellulose oligomers and lignin, wherein the crystallinity of the cellulose-rich solids is at least 70%, wherein $SO_2$ concentration is from about 10 wt % to about 50 wt %, fractionation temperature is from about 130° C. to about 200° C., and fractionation time is from about 30 minutes to about 4 hours;
(c) mechanically treating the cellulose-rich solids to form cellulose fibrils and/or cellulose crystals, thereby generating a nanocellulose material having a crystallinity of at least 70%; and
(d) recovering the nanocellulose material.

Some variations provide a hydrophobic nanocellulose material produced by a process comprising:
(a) providing a lignocellulosic biomass feedstock;
(b) fractionating the feedstock in the presence of an acid, a solvent for lignin, and water, to generate cellulose-rich solids and a liquid containing hemicellulose and lignin, wherein a portion of the lignin deposits onto a surface of the cellulose-rich solids, thereby rendering the cellulose-rich solids at least partially hydrophobic;
(c) mechanically treating the cellulose-rich solids to form cellulose fibrils and/or cellulose crystals, thereby generating a hydrophobic nanocellulose material having a crystallinity of at least 60%; and (d) recovering the hydrophobic nanocellulose material.

Some variations provide a nanocellulose-containing product produced by a process comprising:

(a) providing a lignocellulosic biomass feedstock;
(b) fractionating the feedstock in the presence of an acid, a solvent for lignin, and water, to generate cellulose-rich solids and a liquid containing hemicellulose and lignin;
(c) mechanically treating the cellulose-rich solids to form cellulose fibrils and/or cellulose crystals, thereby generating a nanocellulose material having a crystallinity of at least 60%; and
(d) incorporating at least a portion of the nanocellulose material into a nanocellulose-containing product.

A nanocellulose-containing product that contains the nanocellulose material may be selected from the group consisting of a structural object, a foam, an aerogel, a polymer composite, a carbon composite, a film, a coating, a coating precursor, a current or voltage carrier, a filter, a membrane, a catalyst, a catalyst substrate, a coating additive, a paint additive, an adhesive additive, a cement additive, a paper coating, a thickening agent, a rheological modifier, an additive for a drilling fluid, and combinations or derivatives thereof.

Various embodiments will now be further described, without limitation as to the scope of the invention. These embodiments are exemplary in nature.

In some embodiments, a first process step is "cooking" (equivalently, "digesting") which fractionates the three lignocellulosic material components (cellulose, hemicellulose, and lignin) to allow easy downstream removal. Specifically, hemicelluloses are dissolved and over 50% are completely hydrolyzed; cellulose is separated but remains resistant to hydrolysis; and part of the lignin is sulfonated into water-soluble lignosulfonates.

The lignocellulosic material is processed in a solution (cooking liquor) of aliphatic alcohol, water, and sulfur dioxide. The cooking liquor preferably contains at least 10 wt %, such as at least 20 wt %, 30 wt %, 40 wt %, or 50 wt % of a solvent for lignin. For example, the cooking liquor may contain about 30-70 wt % solvent, such as about 50 wt % solvent. The solvent for lignin may be an aliphatic alcohol, such as methanol, ethanol, 1-propanol, 2-propanol, 1-butanol, 2-butanol, isobutanol, 1-pentanol, 1-hexanol, or cyclohexanol. The solvent for lignin may be an aromatic alcohol, such as phenol or cresol. Other lignin solvents are possible, such as (but not limited to) glycerol, methyl ethyl ketone, or diethyl ether. Combinations of more than one solvent may be employed.

Preferably, enough solvent is included in the extractant mixture to dissolve the lignin present in the starting material. The solvent for lignin may be completely miscible, partially miscible, or immiscible with water, so that there may be more than one liquid phase. Potential process advantages arise when the solvent is miscible with water, and also when the solvent is immiscible with water. When the solvent is water-miscible, a single liquid phase forms, so mass transfer of lignin and hemicellulose extraction is enhanced, and the downstream process must only deal with one liquid stream. When the solvent is immiscible in water, the extractant mixture readily separates to form liquid phases, so a distinct separation step can be avoided or simplified. This can be advantageous if one liquid phase contains most of the lignin and the other contains most of the hemicellulose sugars, as this facilitates recovering the lignin from the hemicellulose sugars.

The cooking liquor preferably contains sulfur dioxide and/or sulfurous acid ($H_2SO_3$). The cooking liquor preferably contains $SO_2$, in dissolved or reacted form, in a concentration of at least 3 wt %, preferably at least 6 wt %, more preferably at least 8 wt %, such as about 9 wt %, 10 wt %, 11 wt %, 12 wt %, 13 wt %, 14 wt %, 15 wt %, 20 wt %, 25 wt %, 30 wt % or higher. The cooking liquor may also contain one or more species, separately from $SO_2$, to adjust the pH. The pH of the cooking liquor is typically about 4 or less.

Sulfur dioxide is a preferred acid catalyst, because it can be recovered easily from solution after hydrolysis. The majority of the $SO_2$ from the hydrolysate may be stripped and recycled back to the reactor. Recovery and recycling translates to less lime required compared to neutralization of comparable sulfuric acid, less solids to dispose of, and less separation equipment. The increased efficiency owing to the inherent properties of sulfur dioxide mean that less total acid or other catalysts may be required. This has cost advantages, since sulfuric acid can be expensive. Additionally, and quite significantly, less acid usage also will translate into lower costs for a base (e.g., lime) to increase the pH following hydrolysis, for downstream operations. Furthermore, less acid and less base will also mean substantially less generation of waste salts (e.g., gypsum) that may otherwise require disposal.

In some embodiments, an additive may be included in amounts of about 0.1 wt % to 10 wt % or more to increase cellulose viscosity. Exemplary additives include ammonia, ammonia hydroxide, urea, anthraquinone, magnesium oxide, magnesium hydroxide, sodium hydroxide, and their derivatives.

The cooking is performed in one or more stages using batch or continuous digestors. Solid and liquid may flow cocurrently or countercurrently, or in any other flow pattern that achieves the desired fractionation. The cooking reactor may be internally agitated, if desired.

Depending on the lignocellulosic material to be processed, the cooking conditions are varied, with temperatures from about 65° C. to 190° C., for example 75° C., 85° C., 95° C., 105° C., 115° C., 125° C., 130° C., 135° C., 140° C., 145° C., 150° C., 155° C., 165° C. or 170° C., and corresponding pressures from about 1 atmosphere to about 15 atmospheres in the liquid or vapor phase. The cooking time of one or more stages may be selected from about 15 minutes to about 720 minutes, such as about 30, 45, 60, 90, 120, 140, 160, 180, 250, 300, 360, 450, 550, 600, or 700 minutes. Generally, there is an inverse relationship between the temperature used during the digestion step and the time needed to obtain good fractionation of the biomass into its constituent parts.

The cooking liquor to lignocellulosic material ratio may be selected from about 1 to about 10, such as about 2, 3, 4, 5, or 6. In some embodiments, biomass is digested in a pressurized vessel with low liquor volume (low ratio of cooking liquor to lignocellulosic material), so that the cooking space is filled with ethanol and sulfur dioxide vapor in equilibrium with moisture. The cooked biomass is washed in alcohol-rich solution to recover lignin and dissolved hemicelluloses, while the remaining pulp is further processed. In some embodiments, the process of fractionating lignocellulosic material comprises vapor-phase cooking of lignocellulosic material with aliphatic alcohol (or other solvent for lignin), water, and sulfur dioxide. See, for example, U.S. Pat. Nos. 8,038,842 and 8,268,125 which are incorporated by reference herein.

A portion or all of the sulfur dioxide may be present as sulfurous acid in the extract liquor. In certain embodiments, sulfur dioxide is generated in situ by introducing sulfurous acid, sulfite ions, bisulfite ions, combinations thereof, or a salt of any of the foregoing. Excess sulfur dioxide, following hydrolysis, may be recovered and reused. In some embodiments, sulfur dioxide is saturated in water (or aqueous solution, optionally with an alcohol) at a first temperature, and the hydrolysis is then carried out at a second, generally higher, temperature. In some embodiments, sulfur dioxide is sub-saturated. In some embodiments, sulfur dioxide is super-saturated. In some embodiments, sulfur dioxide concentration is selected to achieve a certain degree of lignin sulfonation, such as 1%, 2%, 3%, 4%, 5%, 6%, 7%, 8%, 9%, or 10% sulfur content. $SO_2$ reacts chemically with lignin to form stable lignosulfonic acids which may be present both in the solid and liquid phases.

The concentration of sulfur dioxide, additives, and aliphatic alcohol (or other solvent) in the solution and the time of cook may be varied to control the yield of cellulose and hemicellulose in the pulp. The concentration of sulfur dioxide and the time of cook may be varied to control the yield of lignin versus lignosulfonates in the hydrolysate. In some embodiments, the concentration of sulfur dioxide, temperature, and the time of cook may be varied to control the yield of fermentable sugars.

Once the desired amount of fractionation of both hemicellulose and lignin from the solid phase is achieved, the liquid and solid phases are separated. Conditions for the separation may be selected to minimize or enhance the reprecipitation of the extracted lignin on the solid phase. Minimizing lignin reprecipitation is favored by conducting separation or washing at a temperature of at least the glass-transition temperature of lignin (about 120° C.); conversely, enhancing lignin reprecipitation is favored by conducting separation or washing at a temperature less than the glass-transition temperature of lignin.

The physical separation can be accomplished either by transferring the entire mixture to a device that can carry out the separation and washing, or by removing only one of the phases from the reactor while keeping the other phase in place. The solid phase can be physically retained by appropriately sized screens through which liquid can pass. The solid is retained on the screens and can be kept there for successive solid-wash cycles. Alternately, the liquid may be retained and solid phase forced out of the reaction zone, with centrifugal or other forces that can effectively transfer the solids out of the slurry. In a continuous system, countercurrent flow of solids and liquid can accomplish the physical separation.

The recovered solids normally will contain a quantity of lignin and sugars, some of which can be removed easily by washing. The washing-liquid composition can be the same as or different than the liquor composition used during fractionation. Multiple washes may be performed to increase effectiveness. Preferably, one or more washes are performed with a composition including a solvent for lignin, to remove additional lignin from the solids, followed by one or more washes with water to displace residual solvent and sugars from the solids. Recycle streams, such as from solvent-recovery operations, may be used to wash the solids.

After separation and washing as described, a solid phase and at least one liquid phase are obtained. The solid phase contains substantially undigested cellulose. A single liquid phase is usually obtained when the solvent and the water are miscible in the relative proportions that are present. In that case, the liquid phase contains, in dissolved form, most of the lignin originally in the starting lignocellulosic material, as well as soluble monomeric and oligomeric sugars formed in the hydrolysis of any hemicellulose that may have been present. Multiple liquid phases tend to form when the solvent and water are wholly or partially immiscible. The lignin tends to be contained in the liquid phase that contains most of the solvent. Hemicellulose hydrolysis products tend to be present in the liquid phase that contains most of the water.

In some embodiments, hydrolysate from the cooking step is subjected to pressure reduction. Pressure reduction may be done at the end of a cook in a batch digestor, or in an external flash tank after extraction from a continuous digestor, for example. The flash vapor from the pressure reduction may be collected into a cooking liquor make-up vessel. The flash vapor contains substantially all the unreacted sulfur dioxide which may be directly dissolved into new cooking liquor. The cellulose is then removed to be washed and further treated as desired.

A process washing step recovers the hydrolysate from the cellulose. The washed cellulose is pulp that may be used for various purposes (e.g., paper or nanocellulose production). The weak hydrolysate from the washer continues to the final reaction step; in a continuous digestor this weak hydrolysate may be combined with the extracted hydrolysate from the external flash tank. In some embodiments, washing and/or separation of hydrolysate and cellulose-rich solids is conducted at a temperature of at least about 100° C., 110° C., or 120° C. The washed cellulose may also be used for glucose production via cellulose hydrolysis with enzymes or acids.

In another reaction step, the hydrolysate may be further treated in one or multiple steps to hydrolyze the oligomers into monomers. This step may be conducted before, during, or after the removal of solvent and sulfur dioxide. The solution may or may not contain residual solvent (e.g. alcohol). In some embodiments, sulfur dioxide is added or allowed to pass through to this step, to assist hydrolysis. In these or other embodiments, an acid such as sulfurous acid or sulfuric acid is introduced to assist with hydrolysis. In some embodiments, the hydrolysate is autohydrolyzed by heating under pressure. In some embodiments, no additional acid is introduced, but lignosulfonic acids produced during the initial cooking are effective to catalyze hydrolysis of hemicellulose oligomers to monomers. In various embodiments, this step utilizes sulfur dioxide, sulfurous acid, sulfuric acid at a concentration of about 0.01 wt % to 30 wt %, such as about 0.05 wt %, 0.1 wt %, 0.2 wt %, 0.5 wt %, 1 wt %, 2 wt %, 5 wt %, 10 wt %, or 20 wt %. This step may be carried out at a temperature from about 100° C. to 220° C., such as about 110° C., 120° C., 130° C., 140° C., 150° C., 160° C., 170° C., 180° C., 190° C., 200° C., or 210° C. Heating may be direct or indirect to reach the selected temperature.

The reaction step produces fermentable sugars which can then be concentrated by evaporation to a fermentation feedstock. Concentration by evaporation may be accomplished before, during, or after the treatment to hydrolyze oligomers. The final reaction step may optionally be followed by steam stripping of the resulting hydrolysate to remove and recover sulfur dioxide and alcohol, and for removal of potential fermentation-inhibiting side products. The evaporation process may be under vacuum or pressure, from about −0.1 atmospheres to about 10 atmospheres, such as about 0.1 atm, 0.3 atm, 0.5 atm, 1.0 atm, 1.5 atm, 2 atm, 4 atm, 6 atm, or 8 atm.

Recovering and recycling the sulfur dioxide may utilize separations such as, but not limited to, vapor-liquid disengagement (e.g. flashing), steam stripping, extraction, or combinations or multiple stages thereof. Various recycle ratios may be practiced, such as about 0.1, 0.2, 0.3, 0.4, 0.5, 0.6, 0.7, 0.8, 0.9, 0.95, or more. In some embodiments, about 90-99% of initially charged $SO_2$ is readily recovered by distillation from the liquid phase, with the remaining 1-10% (e.g., about 3-5%) of the $SO_2$ primarily bound to dissolved lignin in the form of lignosulfonates.

In a preferred embodiment, the evaporation step utilizes an integrated alcohol stripper and evaporator. Evaporated vapor streams may be segregated so as to have different concentrations of organic compounds in different streams. Evaporator condensate streams may be segregated so as to have different concentrations of organic compounds in different streams. Alcohol may be recovered from the evaporation process by condensing the exhaust vapor and returning to the cooking liquor make-up vessel in the cooking step. Clean condensate from the evaporation process may be used in the washing step.

In some embodiments, an integrated alcohol stripper and evaporator system is employed, wherein aliphatic alcohol is removed by vapor stripping, the resulting stripper product stream is concentrated by evaporating water from the stream, and evaporated vapor is compressed using vapor compression and is reused to provide thermal energy.

The hydrolysate from the evaporation and final reaction step contains mainly fermentable sugars but may also contain lignin depending on the location of lignin separation in the overall process configuration. The hydrolysate may be concentrated to a concentration of about 5 wt % to about 60 wt % solids, such as about 10 wt %, 15 wt %, 20 wt %, 25 wt %, 30 wt %, 35 wt %, 40 wt %, 45 wt %, 50 wt % or 55 wt % solids. The hydrolysate contains fermentable sugars.

Fermentable sugars are defined as hydrolysis products of cellulose, galactoglucomannan, glucomannan, arabinoglucuronoxylans, arabinogalactan, and glucuronoxylans into their respective short-chained oligomers and monomer products, i.e., glucose, mannose, galactose, xylose, and arabinose. The fermentable sugars may be recovered in purified form, as a sugar slurry or dry sugar solids, for example. Any known technique may be employed to recover a slurry of sugars or to dry the solution to produce dry sugar solids.

In some embodiments, the fermentable sugars are fermented to produce biochemicals or biofuels such as (but by no means limited to) ethanol, isopropanol, acetone, 1-butanol, isobutanol, lactic acid, succinic acid, or any other fermentation products. Some amount of the fermentation product may be a microorganism or enzymes, which may be recovered if desired.

When the fermentation will employ bacteria, such as Clostridia bacteria, it is preferable to further process and condition the hydrolysate to raise pH and remove residual $SO_2$ and other fermentation inhibitors. The residual $SO_2$ (i.e., following removal of most of it by stripping) may be catalytically oxidized to convert residual sulfite ions to sulfate ions by oxidation. This oxidation may be accomplished by adding an oxidation catalyst, such as $FeSO_4 \cdot 7H_2O$, that oxidizes sulfite ions to sulfate ions, which is a well-known practice for fermentation to acetone/butanol/ethanol (ABE). Preferably, the residual $SO_2$ is reduced to less than about 100 ppm, 50 ppm, 25 ppm, 10 ppm, 5 ppm, or 1 ppm.

In some embodiments, the process further comprises recovering the lignin as a co-product. The sulfonated lignin may also be recovered as a co-product. In certain embodiments, the process further comprises combusting or gasifying the sulfonated lignin, recovering sulfur contained in the sulfonated lignin in a gas stream comprising reclaimed sulfur dioxide, and then recycling the reclaimed sulfur dioxide for reuse.

The process lignin separation step is for the separation of lignin from the hydrolysate and can be located before or after the final reaction step and evaporation. If located after, then lignin will precipitate from the hydrolysate since alcohol has been removed in the evaporation step. The remaining water-soluble lignosulfonates may be precipitated by converting the hydrolysate to an alkaline condition (pH higher than 7) using, for example, an alkaline earth oxide, preferably calcium oxide (lime). The combined lignin and lignosulfonate precipitate may be filtered. The lignin and lignosulfonate filter cake may be dried as a co-product or burned or gasified for energy production. The hydrolysate from filtering may be recovered and sold as a concentrated sugar solution product or further processed in a subsequent fermentation or other reaction step.

Native (non-sulfonated) lignin is hydrophobic, while lignosulfonates are hydrophilic. Hydrophilic lignosulfonates may have less propensity to clump, agglomerate, and stick to surfaces. Even lignosulfonates that do undergo some condensation and increase of molecular weight, will still have an $HSO_3$ group that will contribute some solubility (hydrophilic).

In some embodiments, the soluble lignin precipitates from the hydrolysate after solvent has been removed in the evaporation step. In some embodiments, reactive lignosulfonates are selectively precipitated from hydrolysate using excess lime (or other base, such as ammonia) in the presence of aliphatic alcohol. In some embodiments, hydrated lime is used to precipitate lignosulfonates. In some embodiments, part of the lignin is precipitated in reactive form and the remaining lignin is sulfonated in water-soluble form.

The process fermentation and distillation steps are intended for the production of fermentation products, such as alcohols or organic acids. After removal of cooking chemicals and lignin, and further treatment (oligomer hydrolysis), the hydrolysate contains mainly fermentable sugars in water solution from which any fermentation inhibitors have been preferably removed or neutralized. The hydrolysate is fermented to produce dilute alcohol or organic acids, from 1 wt % to 20 wt % concentration. The dilute product is distilled or otherwise purified as is known in the art.

When alcohol is produced, such as ethanol, some of it may be used for cooking liquor makeup in the process cooking step. Also, in some embodiments, a distillation column stream, such as the bottoms, with or without evaporator condensate, may be reused to wash cellulose. In some embodiments, lime may be used to dehydrate product alcohol. Side products may be removed and recovered from the hydrolysate. These side products may be isolated by processing the vent from the final reaction step and/or the condensate from the evaporation step. Side products include furfural, hydroxymethyl furfural (HMF), methanol, acetic acid, and lignin-derived compounds, for example.

The glucose may be fermented to an alcohol, an organic acid, or another fermentation product. The glucose may be used as a sweetener or isomerized to enrich its fructose content. The glucose may be used to produce baker's yeast. The glucose may be catalytically or thermally converted to various organic acids and other materials.

When hemicellulose is present in the starting biomass, all or a portion of the liquid phase contains hemicellulose sugars and soluble oligomers. It is preferred to remove most of the lignin from the liquid, as described above, to produce a fermentation broth which will contain water, possibly some of the solvent for lignin, hemicellulose sugars, and various minor components from the digestion process. This fermentation broth can be used directly, combined with one or more other fermentation streams, or further treated. Further treatment can include sugar concentration by evaporation; addition of glucose or other sugars (optionally as obtained from cellulose saccharification); addition of various nutrients such as salts, vitamins, or trace elements; pH adjustment; and removal of fermentation inhibitors such as acetic acid and phenolic compounds. The choice of conditioning steps should be specific to the target product(s) and microorganism(s) employed.

In some embodiments, hemicellulose sugars are not fermented but rather are recovered and purified, stored, sold, or converted to a specialty product. Xylose, for example, can be converted into xylitol.

A lignin product can be readily obtained from a liquid phase using one or more of several methods. One simple technique is to evaporate off all liquid, resulting in a solid lignin-rich residue. This technique would be especially advantageous if the solvent for lignin is water-immiscible. Another method is to cause the lignin to precipitate out of solution. Some of the ways to precipitate the lignin include (1) removing the solvent for lignin from the liquid phase, but not the water, such as by selectively evaporating the solvent from the liquid phase until the lignin is no longer soluble; (2) diluting the liquid phase with water until the lignin is no longer soluble; and (3) adjusting the temperature and/or pH of the liquid phase. Methods such as centrifugation can then be utilized to capture the lignin. Yet another technique for removing the lignin is continuous liquid-liquid extraction to selectively remove the lignin from the liquid phase, followed by removal of the extraction solvent to recover relatively pure lignin.

Lignin produced in accordance with the invention can be used as a fuel. As a solid fuel, lignin is similar in energy content to coal. Lignin can act as an oxygenated component in liquid fuels, to enhance octane while meeting standards as a renewable fuel. The lignin produced herein can also be used as polymeric material, and as a chemical precursor for producing lignin derivatives. The sulfonated lignin may be sold as a lignosulfonate product, or burned for fuel value.

The present invention also provides systems configured for carrying out the disclosed processes, and compositions produced therefrom. Any stream generated by the disclosed processes may be partially or completed recovered, purified or further treated, and/or marketed or sold.

Certain nanocellulose-containing products provide high transparency, good mechanical strength, and/or enhanced gas (e.g., $O_2$ or $CO_2$) barrier properties, for example. Certain nanocellulose-containing products containing hydrophobic nanocellulose materials provided herein may be useful as anti-wetting and anti-icing coatings, for example.

Due to the low mechanical energy input, nanocellulose-containing products provided herein may be characterized by fewer defects that normally result from intense mechanical treatment.

Some embodiments provide nanocellulose-containing products with applications for sensors, catalysts, antimicrobial materials, current carrying and energy storage capabilities. Cellulose nanocrystals have the capacity to assist in the synthesis of metallic and semiconducting nanoparticle chains.

Some embodiments provide composites containing nanocellulose and a carbon-containing material, such as (but not limited to) lignin, graphite, graphene, or carbon aerogels.

Cellulose nanocrystals may be coupled with the stabilizing properties of surfactants and exploited for the fabrication of nanoarchitectures of various semiconducting materials.

The reactive surface of —OH side groups in nanocellulose facilitates grafting chemical species to achieve different surface properties. Surface functionalization allows the tailoring of particle surface chemistry to facilitate self-assembly, controlled dispersion within a wide range of matrix polymers, and control of both the particle-particle and particle-matrix bond strength. Composites may be transparent, have tensile strengths greater than cast iron, and have very low coefficient of thermal expansion. Potential applications include, but are not limited to, barrier films, antimicrobial films, transparent films, flexible displays, reinforcing fillers for polymers, biomedical implants, pharmaceuticals, drug delivery, fibers and textiles, templates for electronic components, separation membranes, batteries, supercapacitors, electroactive polymers, and many others.

Other nanocellulose applications suitable to the present invention include reinforced polymers, high-strength spun fibers and textiles, advanced composite materials, films for barrier and other properties, additives for coatings, paints, lacquers and adhesives, switchable optical devices, pharmaceuticals and drug delivery systems, bone replacement and tooth repair, improved paper, packaging and building products, additives for foods and cosmetics, catalysts, and hydrogels.

Aerospace and transportation composites may benefit from high crystallinity. Automotive applications include nanocellulose composites with polypropylene, polyamide (e.g. Nylons), or polyesters (e.g. PBT).

Nanocellulose materials provided herein are suitable as strength-enhancing additives for renewable and biodegradable composites. The cellulosic nanofibrillar structures may function as a binder between two organic phases for improved fracture toughness and prevention of crack formation for application in packaging, construction materials, appliances, and renewable fibers.

Nanocellulose materials provided herein are suitable as transparent and dimensional stable strength-enhancing additives and substrates for application in flexible displays, flexible circuits, printable electronics, and flexible solar panels. Nanocellulose is incorporated into the substrate-sheets are formed by vacuum filtration, dried under pressure and calandered, for example. In a sheet structure, nanocellulose acts as a glue between the filler aggregates. The formed calandered sheets are smooth and flexible.

Nanocellulose materials provided herein are suitable for composite and cement additives allowing for crack reduction and increased toughness and strength. Foamed, cellular nanocellulose-concrete hybrid materials allow for lightweight structures with increased crack reduction and strength.

Strength enhancement with nanocellulose increases both the binding area and binding strength for application in high strength, high bulk, high filler content paper and board with enhanced moisture and oxygen barrier properties. The pulp and paper industry in particular may benefit from nanocellulose materials provided herein.

Nanofibrillated cellulose nanopaper has a higher density and higher tensile mechanical properties than conventional paper. It can also be optically transparent and flexible, with low thermal expansion and excellent oxygen barrier characteristics. The functionality of the nanopaper can be further broadened by incorporating other entities such as carbon nanotubes, nanoclay or a conductive polymer coating.

Porous nanocellulose may be used for cellular bioplastics, insulation and plastics and bioactive membranes and filters. Highly porous nanocellulose materials are generally of high interest in the manufacturing of filtration media as well as for biomedical applications, e.g., in dialysis membranes.

Nanocellulose materials provided herein are suitable as coating materials as they are expected to have a high oxygen barrier and affinity to wood fibers for application in food packaging and printing papers.

Nanocellulose materials provided herein are suitable as additives to improve the durability of paint, protecting paints and varnishes from attrition caused by UV radiation.

Nanocellulose materials provided herein are suitable as thickening agents in food and cosmetics products. Nanocellulose can be used as thixotropic, biodegradable, dimensionally stable thickener (stable against temperature and salt addition). Nanocellulose materials provided herein are suitable as a Pickering stabilizer for emulsions and particle stabilized foam.

The large surface area of these nanocellulose materials in combination with their biodegradability makes them attractive materials for highly porous, mechanically stable aerogels. Nanocellulose aerogels display a porosity of 95% or higher, and they are ductile and flexible.

Drilling fluids are fluids used in drilling in the natural gas and oil industries, as well as other industries that use large drilling equipment. The drilling fluids are used to lubricate, provide hydrostatic pressure, and to keep the drill cool, and the hole as clean as possible of drill cuttings. Nanocellulose materials provided herein are suitable as additives to these drilling fluids.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

EXAMPLES

High-impact polystyrene was blended using a twin-screw extruder with 0.7 wt % nanocellulose, in the form of hydrophobic lignin-coated cellulose nanocrystals (L-CNC) and hydrophobic lignin-coated cellulose nanofibrils (L-CNF). The polystyrene is from LG chemical, and the nanocellulose materials as are described herein. The polystyrene/nanocellulose melt was processed at about 180-210° C.

IZOD impact resistance was measured by Standard ASTM D256. Tensile strength was measured by Standard ASTM D638. Flex modulus was measured by Standard ASTM D790.

Compared to a control with no nanocellulose, the IZOD impact resistance was 84% improved for L-CNC and 77% improved for L-CNF. The tensile strength was 14% improved for L-CNC and 18% improved for L-CNF. The elongation at break was 38% higher for L-CNC and 52% higher for L-CNF. The flex modulus was slightly lower compared to control (7% and 4% lower for L-CNC and L-CNF, respectively).

Nanocellulose gives a significant and surprisingly large improvement to impact-grade polystyrene at very low loadings. Even larger benefit may be realized at higher nanocellulose loadings.

What is claimed is:

1. A polymer composite comprising polystyrene and hydrophobic, lignin-coated nanocellulose.

2. The polymer composite of claim 1, wherein said composite contains about 0.01 wt % to about 10 wt % of said nanocellulose.

3. The polymer composite of claim 2, wherein said composite contains about 0.05 wt % to about 5 wt % of said nanocellulose.

4. The polymer composite of claim 3, wherein said composite contains about 0.1 wt % to about 2 wt % of said nanocellulose.

5. The polymer composite of claim 1, wherein said nanocellulose is obtained from a biomass-fractionation process comprising fractionation of lignocellulosic biomass using an acid catalyst, a solvent for lignin, and water, to generate lignin-coated cellulose, followed by mechanically refining said lignin-coated cellulose to produce said nanocellulose.

6. The polymer composite of claim 1, wherein said nanocellulose includes cellulose nanocrystals and/or cellulose nanofibrils.

7. The polymer composite of claim 1, wherein said polymer composite is a polymer melt.

8. The polymer composite of claim 1, wherein said polymer composite is a finished polymer material.

9. The polymer composite of claim 1, wherein said composite is characterized by IZOD impact resistance that is at least 50% higher compared to said polystyrene alone.

* * * * *